(12) United States Patent
Kalgren et al.

(10) Patent No.: US 7,457,663 B2
(45) Date of Patent: *Nov. 25, 2008

(54) CARDIAC RHYTHM MANAGEMENT SYSTEM PROVIDING CONTROL OF PACING FEATURES WITH A REDUCED NUMBER OF VARIABLES

(75) Inventors: James Kalgren, Lino Lakes, MN (US); Rene H. Wentkowski, White Bear Lake, MN (US); Jeffrey E. Stahmann, Ramsey, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 446 days.

This patent is subject to a terminal disclaimer.

(21) Appl. No.: 10/652,973

(22) Filed: Aug. 29, 2003

(65) Prior Publication Data
US 2004/0143305 A1 Jul. 22, 2004

Related U.S. Application Data

(63) Continuation of application No. 09/739,091, filed on Dec. 15, 2000, now Pat. No. 6,618,618.

(51) Int. Cl.
*A61N 1/36* (2006.01)
(52) U.S. Cl. .............................. 607/9; 607/30
(58) Field of Classification Search .................. 607/18, 607/19, 4, 7, 9
See application file for complete search history.

(56) References Cited

U.S. PATENT DOCUMENTS

| | | | | |
|---|---|---|---|---|
| 4,208,008 A | 6/1980 | Smith | ........................... | 371/15 |
| 4,378,020 A | 3/1983 | Nappholz et al. | ..... | 128/419 PG |
| 4,432,360 A | 2/1984 | Mumford et al. | ...... | 128/419 PG |
| 4,872,459 A | 10/1989 | Pless et al. | .................. | 128/419 |
| 5,607,460 A | 3/1997 | Kroll et al. | ..................... | 607/30 |
| 5,716,382 A | 2/1998 | Snell | ........................... | 607/30 |
| 5,725,559 A | 3/1998 | Alt et al. | ....................... | 607/5 |

(Continued)

OTHER PUBLICATIONS

"U.S. Appl. No. 09/729,091 Non Final Office Action mailed Dec. 12, 2002", 6 pgs.

(Continued)

*Primary Examiner*—Scott M Getzow
(74) *Attorney, Agent, or Firm*—Schwegman, Lundberg & Woessner, P.A.

(57) ABSTRACT

A cardiac rhythm management system includes techniques for reducing the number of programmable variables associated with maximum pacing rate so that fewer variables are programmed and a reduction in possible parameter conflict is achieved. In an embodiment, a maximum pacing rate parameter replaces a plurality of conventional, separately programmable pacing parameters. For example, maximum tracking rate, maximum sensor rate, rate smoothing maximum pacing rate, atrial pacing preference maximum pacing rate, and ventricular rate regulation maximum pacing rate are replaced by a single maximum pacing rate with, if necessary, a sensor offset and an atrial pacing preference offset. In another example, rate smoothing maximum pacing rate, biventricular trigger maximum pacing rate and ventricular rate regulation maximum pacing rate are replaced by a single maximum pacing rate.

19 Claims, 4 Drawing Sheets

U.S. PATENT DOCUMENTS

| | | | |
|---|---|---|---|
| 5,749,907 A | 5/1998 | Mann | 607/27 |
| 5,836,989 A | 11/1998 | Shelton | 607/27 |
| 6,055,454 A * | 4/2000 | Heemels | 607/18 |
| 6,119,040 A | 9/2000 | Chirife | 607/18 |
| 6,256,536 B1 | 7/2001 | Kramer | 607/9 |
| 6,289,248 B1 | 9/2001 | Conley et al. | 607/59 |
| 6,618,618 B2 * | 9/2003 | Kalgren et al. | 607/9 |

OTHER PUBLICATIONS

"U.S. Appl. No. 09/729,091 Notice of Allowance mailed Apr. 4, 2003", 5 pgs.

"U.S. Appl. No. 09/729,091 Response filed Mar. 12, 2003 to Non Final Office Action mailed Dec. 12, 2002", 11 pgs.

* cited by examiner

CARDIAC RHYTHM MANAGEMENT SYSTEM PROVIDING CONTROL OF PACING FEATURES WITH A REDUCED NUMBER OF VARIABLES

CROSS-REFERENCE TO RELATED APPLICATION(S)

This application is a continuation of U.S. patent application Ser. No. 09/739,091, filed on Dec. 15, 2000, now issued as U.S. Pat. No. 6,618,618, the specification of which is incorporated herein by reference.

FIELD OF THE INVENTION

The present system relates generally to cardiac rhythm management systems and more particularly to a system reducing the number of variables associated with the maximum pacing rate.

BACKGROUND

Cardiac rhythm management systems provide therapy to a patient's heart to correct various forms of arrhythmias, such as tachyarrhythmias and bradyarrhythmias. One type of these systems includes an implantable cardiac rhythm management ("CRM") device and a programmer for programming the CRM device. As the understanding of various types of arrhythmias has grown since the inception of CRM devices over two decades ago, so has the need to provide a greater variety of therapies with the CRM device. This greater variety of therapies allows a physician to closely tailor the therapy provided by the device to the specific needs of the patient by programming various parameters of the CRM device. However, the number of programmable variables in CRM devices has grown along with the number and complexity of therapies. Accordingly, the physician must use the programmer to program numerous parameters of the CRM device to achieve the desired therapy. When it is decided that a certain therapy should be altered, a corresponding programmable parameter is changed. The medical care provider must change this programmable parameter and all related parameters. In some programmers, different parameters are displayed and accessible on different screens of the programmer. Accordingly, the level of complexity and knowledge of the CRM device and the programmer, which the medical care provider must understand when changing any programmable parameter so that all related parameters are appropriately changed, has increased with recent CRM devices. Consequently, there is a need in the field of CRM systems to simplify the programming of the CRM device by reducing the number of programmable variables.

SUMMARY OF THE INVENTION

The present system provides, among other things, a cardiac rhythm management system including techniques for reducing the number of programmable parameters associated with a single variable. In one embodiment, a plurality of maximum pacing rates are combined into a single maximum pacing rate parameter. This maximum pacing rate parameter is used by different therapy processes. In another embodiment, the system includes setting a single maximum pacing rate with offsets therefrom for select pacing features.

In another embodiment, the system includes a method of programming a cardiac rhythm management device with a single maximum pacing rate for a plurality of therapies.

Other aspects of the invention will be apparent on reading the following detailed description of the invention and viewing the drawings that form a part thereof.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present method and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

Figure 1:
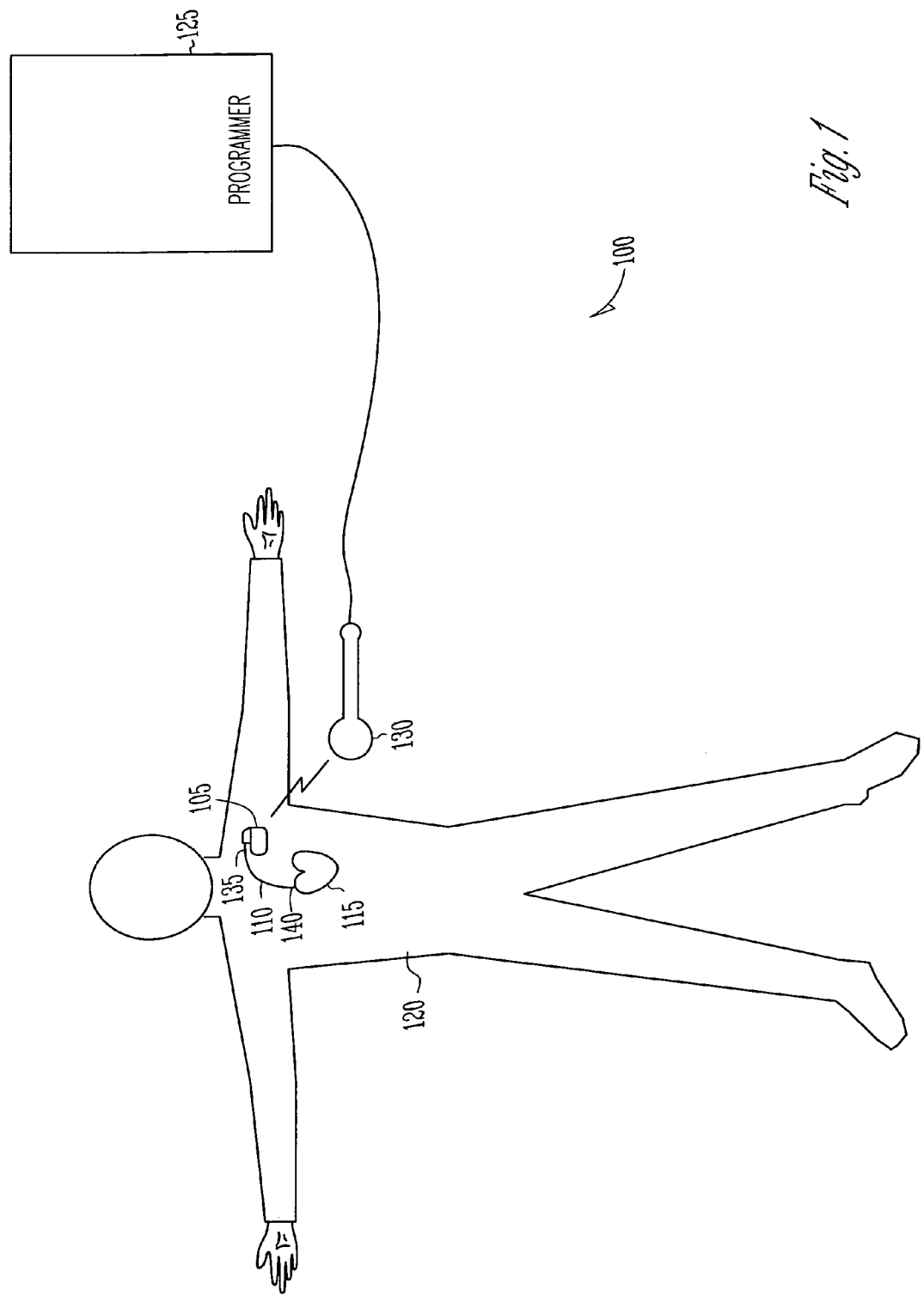
FIG. 1 is a schematic drawing illustrating generally one embodiment of portions of a cardiac rhythm management system and an environment in which it is used.

FIG. 1 is a schematic drawing illustrating, by way of example, one embodiment of portions of a cardiac rhythm management system 100 and an environment in which it is used. In FIG. 1, system 100 includes an implantable cardiac rhythm management device 105, which is coupled by an intravascular endocardial lead 110, or other lead, to a heart 115 of patient 120. Device 105 typically contains electronic circuitry. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
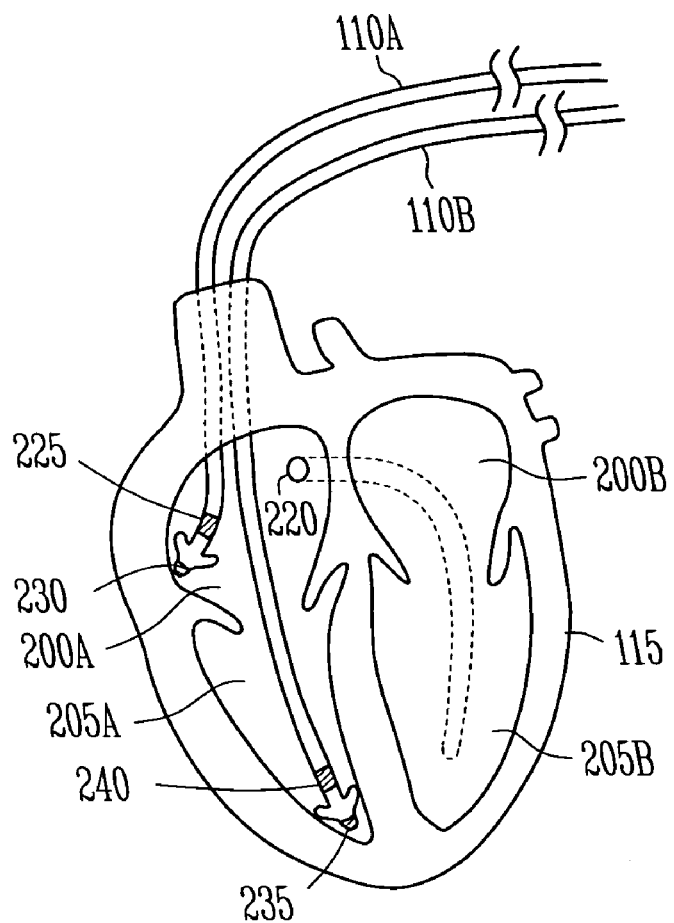
FIG. 2 is a schematic drawing illustrating one embodiment of a cardiac rhythm management device coupled by leads to a heart.

FIG. 2 is a schematic drawing illustrating, by way of example, one embodiment of device 105 coupled by leads 110A-B to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near an atrium 200 of heart 115, such as ring electrode 225 and tip electrode 230, for sensing signals and/or delivering pacing therapy (atrial pacing) to the atrium 200. Lead 110A optionally also includes additional electrodes, such as for delivering atrial and/or ventricular cardioversion/defibrillation and/or pacing therapy to heart 115.

In FIG. 2, ventricular lead 110B includes one or more electrodes, such as tip electrode 235 and ring electrode 240, for delivering sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed housing, which is sometimes referred to as a can. Additional electrodes may be located on the can, or on an insulating header, or on other portions of device 105, for providing pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. The present method and apparatus will work in a variety of configurations and with a variety of electrical contacts or "electrodes."

Figure 3:
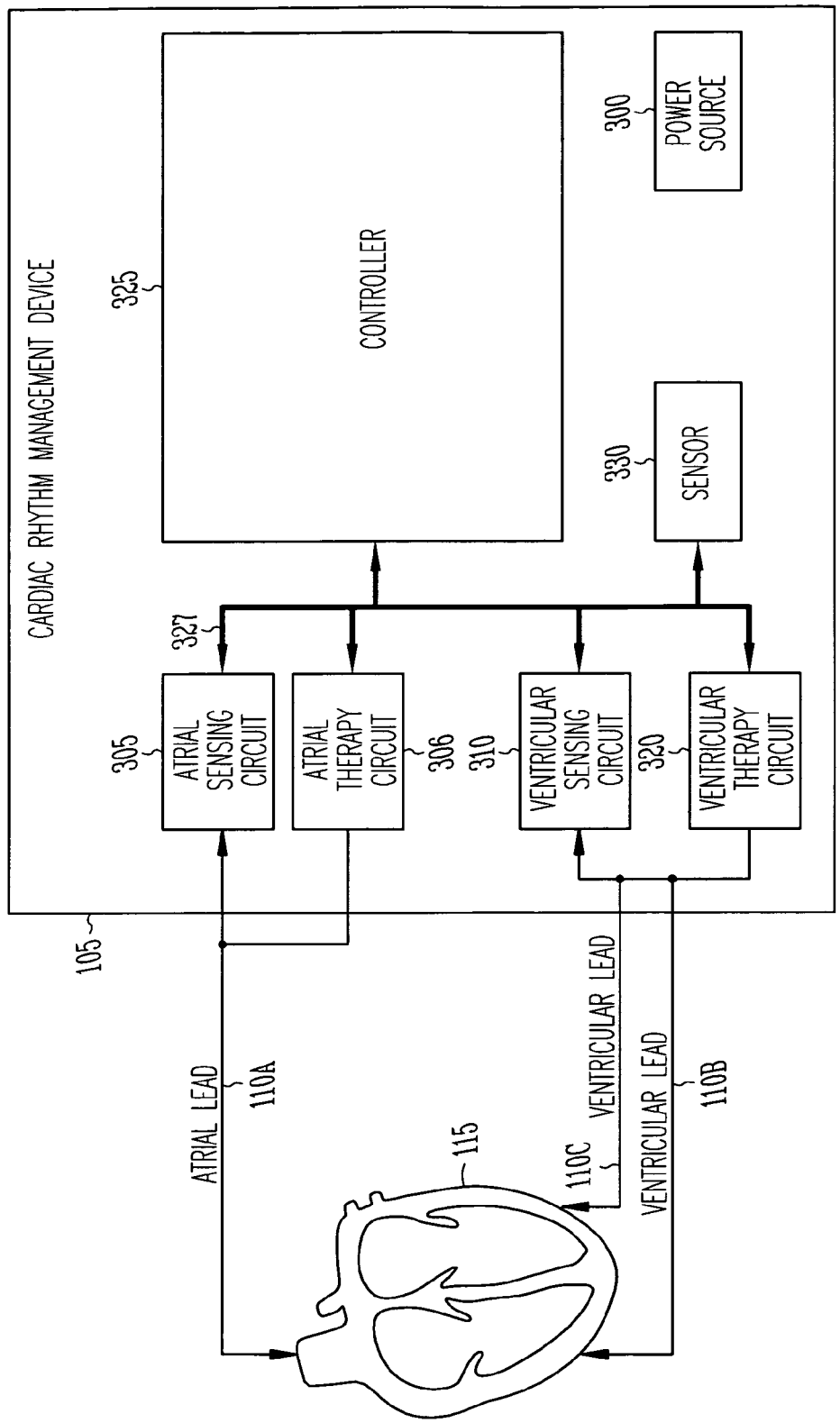
FIG. 3 is a schematic diagram illustrating generally one embodiment of portions of a cardiac rhythm management device coupled to a heart.

FIG. 3 is a schematic diagram illustrating generally, by way of example, one embodiment of portions of device 105, which is coupled to heart 115. Device 105 includes a power source 300, an atrial sensing circuit 305, an atrial therapy circuit 306, a ventricular sensing circuit 310, a ventricular therapy circuit 320, and a controller 325.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals. Such signals provided to controller 325 indicate, among other things, the presence of atrial fibrillation.

Atrial therapy circuit 306 provides atrial pacing therapy, as appropriate, to electrodes located at or near one of the atriums 200 of heart 115 for obtaining resulting evoked atrial depolarizations. In one embodiment, atrial therapy circuit 306 also provides cardioversion/defibrillation therapy, as appropriate, to electrodes located at or near one, or both, of the atriums 205 of heart 115, for terminating atrial fibrillation and/or other atrial arrhythmias.

Ventricular sensing circuit 310 is coupled by ventricular leads 110B, 110C to heart 115 for receiving, sensing, and/or detecting electrical ventricular heart signals, such as ventricular activations (also referred to as ventricular depolarizations or R-waves), which correspond to ventricular contractions. Ventricular lead 110C is similar to lead 110B described above. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Ventricular sensing circuit 310 provides one or more signals to controller 325, via node/bus 327, based on the received ventricular heart signals. Such signals provided to controller 325 indicate, among other things, the presence of ventricular depolarizations, whether regular or irregular in rhythm.

Ventricular therapy circuit 320 provides ventricular pacing therapy, as appropriate, to electrodes located at or near one of the ventricles 205 of heart 115 for obtaining resulting evoked ventricular depolarizations. In one embodiment, ventricular therapy circuit 320 also provides cardioversion/defibrillation therapy, as appropriate, to electrodes located at or near one, or both, of the ventricles 205 of heart 115, for terminating ventricular fibrillation and/or other ventricular tachyarrhythmias.

Controller 325 controls the delivery of therapy by ventricular therapy circuit 320 and/or other circuits, based on heart activity signals received from atrial sensing circuit 305 and ventricular sensing circuit 310. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware. In an embodiment, the controller 325 includes a memory in which is stored default parameters, which are used by the programmer to control various therapies. One such default parameter may be a maximum pacing rate.

In general terms, sensing circuits 305 and 310 sense electrical signals from heart tissue in contact with the catheter leads 110A-C to which these sensing circuits 305 and 310 are coupled. Sensing circuits 305 and 310 and/or controller 325 process these sensed signals. Based on these sensed signals, controller 325 issues control signals to therapy circuits, such as atrial therapy circuit 306 and/or ventricular therapy circuit 320, if necessary, for the delivery of electrical energy (e.g., pacing and/or defibrillation pulses) to the appropriate electrodes of leads 110A-C. Controller 325 may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Figure 4:
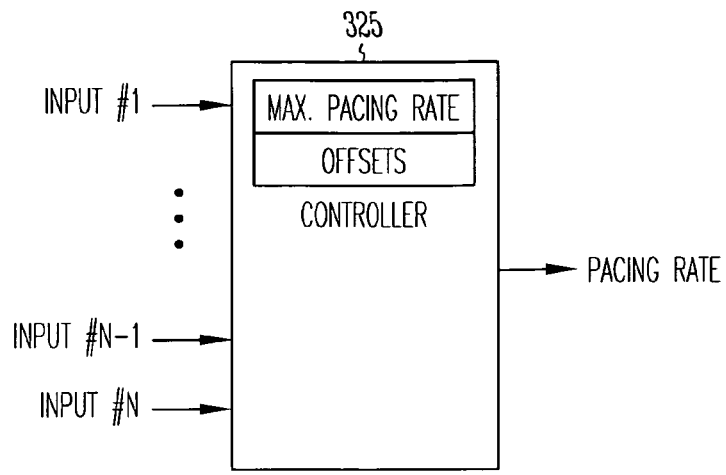
FIG. 4 is a schematic diagram illustrating generally one embodiment of a controller.

FIG. 4 is a schematic diagram illustrating generally, by way of example, controller 325 that includes several different inputs to modify various programmable parameters of the cardiac rhythm management device 105. However, only one of the inputs is a maximum pacing rate. Accordingly, in an embodiment controller 325 limits the maximum pacing rate for all of the therapies using the single maximum pacing rate input. For example, ventricle and atrium pacing are limited by the single maximum pacing rate. In another embodiment, rate smoothing, biventricular triggered pacing and ventricular rate regulation are limited by the single maximum pacing rate. Ventricular rate regulation provides nearly continuous (i.e., to the desired degree) biventricular pacing when the ventricular heart rate is substantially constant. In another embodiment, tracking rate, sensor rate, rate smoothing, atrial pacing preference, ventricular rate regulation are limited by the single maximum pacing rate. The maximum tracking rate limits how quickly the ventricle is paced. The maximum sensor rate limits how fast a heart is paced based on sensed variables. The maximum rate smoothing prevents the pacing rate interval from changing to quickly from one cycle to the next. It will be understood that the single maximum pacing rate is used to limit the pacing rate of more than one therapy, for example any two of the therapies listed herein. Accordingly, a medical care provider need only input the maximum pacing rate into the programmer 125 once. Programmer 125 transmits the maximum pacing rate to the CRM device 105. Limited by the single maximum pacing rate and based on other inputs, controller 325 provides an output indication of pacing rate as a control signal delivered to a therapy circuit, such as to atrial therapy circuit 306 or ventricular therapy circuit 320. Atrial or ventricular therapy circuit 306 or 320 issues pacing pulses based on one or more such control signals received from controller 325. Control of the pacing rate may be performed by controller 325, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device 105.

In an embodiment of controller 325, the controller is configured to provide biventricular triggered pacing, which is pacing one or both ventricles based on sensed ventricular contractions in one ventricle and triggers ventricular pace in the other or both ventricles. Controller 325 uses the maximum pacing rate to limit how fast it will pace one or both of the ventricles to treat hemodynamic dysfunction, e.g. bundle branch blocks or slow conduction in a portion of the ventricles, so as to improve the efficiency of the heart.

In another embodiment of controller 325, it is configured to receive maximum pacing rate offsets from programmer 125. In some therapies it is necessary to deviate from the single maximum pacing rate, for example atrial pacing preference such that an appropriate limit on how fast the atrium is paced by CRM device 105 or an appropriate limit as to when the atrium is paced by CRM device 105 are respectively imposed.

Figure 5:
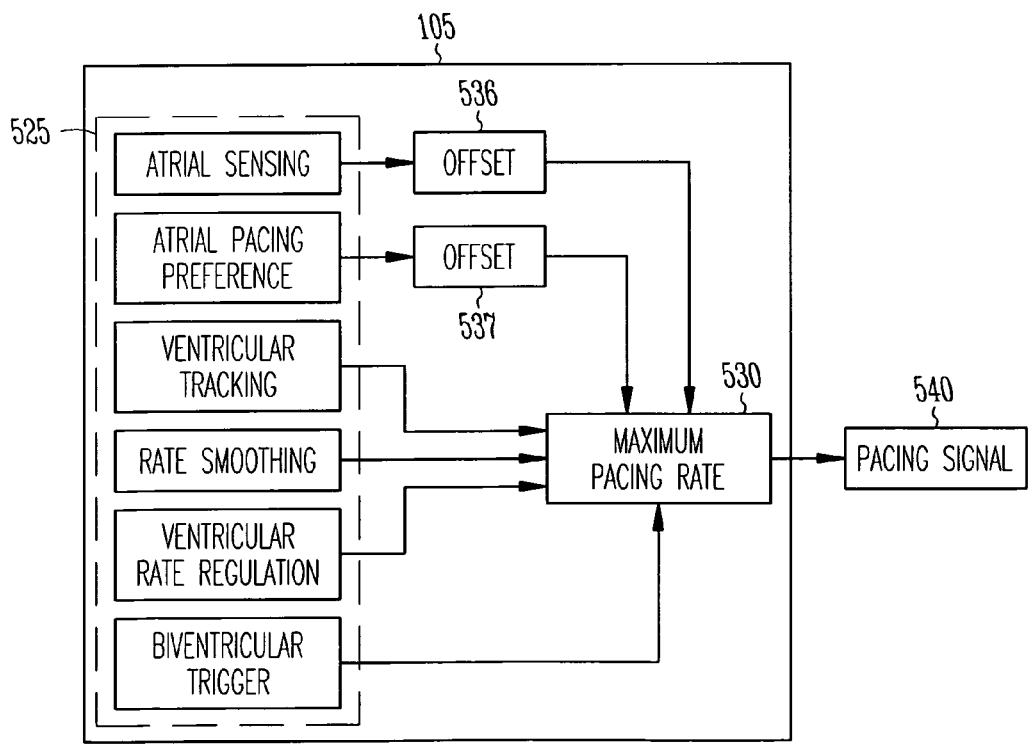
FIG. 5 is a schematic diagram illustrating an embodiment of the cardiac rhythm management device.

FIG. 5 shows an embodiment of CRM device 105 having hardware, e.g. circuitry, and software for a plurality of possible therapies 525. Each of the possible therapies is adapted to pace a patient's heart. Each therapy is limited by a single maximum pacing rate 530. The maximum pacing rate 530 is a default maximum pacing rate stored in the controller or a downloaded maximum pacing rate, for example downloaded by programmer 125. Some therapies, e.g. atrial pacing preference, require a different maximum pacing rate than the other therapies. Offsets include a percentage offset from the maximum pacing rate, a fractional offset, and a discrete number offset. The offsets can increase or decrease the pacing rate from the maximum pacing rate. Additionally, the offsets can be different for different therapies. Offsets 536, 537 are loaded into the CRM device 105, for example by programmer 125. These offsets 536, 537 are used by CRM device 105 to increase or decrease the maximum pacing rate for the therapies requiring a different maximum pacing rate. The CRM device 105 outputs a pacing signal 540 that is limited by the maximum pacing rate 530 and, if any, offsets 536, 537.

In one embodiment of the system 100, programmer 125 stores which of the possible therapies of a given CRM device 105 might require an offset. The programmer 125 prompts the user for an offset when these therapies are activated in the CRM device 105. It is within the scope of the present invention for the offset to be an integer which is added or subtracted from the single maximum pacing rate, or a fraction which is multiplied times the single maximum pacing rate.

CONCLUSION

Previous CRM devices had separate maximum pacing rates for each therapy. CRM devices provide a plurality of therapies and hence a user must program a corresponding plurality of maximum pacing rates. For example, such a CRM device would include a first input providing rate smoothing maximum pacing rate, a second input providing biventricular trigger maximum pacing rate, and a third input providing a ventricular rate regulation maximum pacing rate. The inputs may further include maximum tracking rate, maximum sensor rate, rate smoothing maximum pacing rate, atrial pacing preference maximum pacing rate, ventricular rate regulation maximum pacing rates. A physician must accordingly program all of these various maximum pacing rates so that the CRM device will administer the appropriate therapy which is limited by a specific maximum pacing rate corresponding to the therapy. However, due to the numerous different maximum pacing rates a physician may overlook one of the maximum pacing rate parameters when programming the CRM device, especially if the programmer accesses the different variables on different display screens. This could result in the CRM device administering unintended therapy to a patient by the CRM device relying on an unintended maximum pacing rate that was not correctly set.

The above-described system provides, among other things, a cardiac rhythm management system including techniques for reducing the number of variables which must be adjusted to reduce potential conflicts parameters. In an embodiment, the parameters are maximum pacing rates. This embodiment attempts to reduce the occurrence of users failing to adjust all maximum pacing rates when it is necessary to do so.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac rhythm management system, comprising:
   at least one module; and
   a communication unit configured to transmit to the at least one module a single maximum pacing rate signal associated by the at least one module with a single maximum pacing rate for a plurality of pacing processes and an offset signal associated by the at least one module with an offset from the single maximum pacing rate for a pacing process of the plurality of pacing processes, wherein the transmitted maximum pacing rate limits at least two of the plurality of pacing processes and the transmitted maximum pacing rate, as offset by the offset, limits the pacing process of the plurality of pacing processes.

2. The system of claim 1, wherein said plurality of pacing processes includes at least one of ventricular tracking, rate smoothing, tracking rate, sensor rate, ventricular rate regulation, and biventricular triggering, and wherein said plurality of pacing processes includes at least one of atrial sensing and atrial pacing preference.

3. The system of claim 1, wherein said pacing process includes atrial pacing preference, wherein said communication unit downloads the offset signal including an atrial pacing preference offset to offset said maximum pacing rate to determine a maximum atrial pacing preference rate.

4. The system of claim 1, wherein the communication unit is adapted to wirelessly transmit the offset.

5. The system of claim 1, wherein the communication unit is adapted to prompt a user to input the offset.

6. The system of claim 1, wherein the communication unit is adapted to transmit an atrial pacing preference offset.

7. The system of claim 6, wherein the atrial pacing preference offset is a fraction of the single maximum pacing rate.

8. The system of claim 6, wherein the atrial pacing preference offset is a percentage of the single maximum pacing rate.

9. The system of claim 6, wherein the atrial pacing preference offset is a discrete number offset of the single maximum pacing rate.

10. The system of claim 1, further comprising a memory adapted to store which of the plurality of pacing processes requires an offset from the single maximum pacing rate.

11. The system of claim 10, wherein the memory is adapted to store a default single maximum pacing rate.

12. The system of claim 1, wherein the communication unit is adapted to receive the single maximum pacing rate as an input.

13. The system of claim 1, wherein the communication unit includes a telemetry device.

14. A cardiac rhythm management system, comprising:
at least one module;
a communication unit configured to transmit to the at least one module a single maximum pacing rate signal associated by the at least one module with a single maximum pacing rate for a plurality of pacing processes and an offset signal associated by the at least one module with an offset from the single maximum pacing rate for a pacing process of the plurality of pacing processes, wherein the transmitted maximum pacing rate limits at least two of the plurality of pacing processes and the transmitted maximum pacing rate, as offset by the offset, limits the pacing process of the plurality of pacing processes; and
a memory adapted to store which of the plurality of pacing processes requires the offset from the single maximum pacing rate.

15. The system of claim 14, wherein said plurality of pacing processes includes at least one of ventricular tracking, rate smoothing, tracking rate, sensor rate, ventricular rate regulation, and biventricular triggering, and wherein said plurality of pacing processes includes at least one of atrial sensing and atrial pacing preference.

16. The system of claim 15, wherein said pacing process includes atrial pacing preference, wherein said communication unit downloads the offset signal including an atrial pacing preference offset to offset said maximum pacing rate to determine a maximum atrial pacing preference rate.

17. A cardiac rhythm management system, comprising:
at least one module;
a wireless communication unit configured to communicate to the at least one module a single maximum pacing rate signal associated by the at least one module with a single maximum pacing rate for a plurality of pacing processes and an offset signal associated by the at least one module with an offset from the single maximum pacing rate for a pacing process of the plurality of pacing processes, wherein the transmitted maximum pacing rate limits at least two of the plurality of pacing processes and the transmitted maximum pacing rate, as offset by the offset, limits the pacing process of the plurality of pacing processes; and
a memory adapted to store which of the plurality of pacing processes requires the offset from the single maximum pacing rate.

18. The system of claim 17, wherein said plurality of pacing processes includes at least one of ventricular tracking, rate smoothing, tracking rate, sensor rate, ventricular rate regulation, and biventricular triggering, and at least one of atrial sensing and atrial pacing preference.

19. The system of claim 17, wherein said pacing process includes atrial pacing preference, wherein said communication unit downloads the offset signal including an atrial pacing preference offset to offset said maximum pacing rate to determine a maximum atrial pacing preference rate.

* * * * *